United States Patent [19]

Cattanach

[11] Patent Number: 4,848,363

[45] Date of Patent: Jul. 18, 1989

[54] VALVED VAGINAL COLLECTION DEVICE

[75] Inventor: John F. Cattanach, Hawthorn, Australia

[73] Assignee: Chattan Nominees Pty, Ltd., Hawthorn, Australia

[21] Appl. No.: 53,191

[22] Filed: May 8, 1987

[30] Foreign Application Priority Data

Sep. 13, 1985 [AU] Australia ............... PH2413
Sep. 12, 1986 [AU] Australia ............ PCT/AU86/00270

[51] Int. Cl.⁴ ............................................. A61F 13/00
[52] U.S. Cl. ...................................... 128/834; 128/840
[58] Field of Search ........................... 604/327–331, 604/358, 366, 327–331, 358, 366; 128/132 R, 138 R, 834, 839–841

[56] References Cited

U.S. PATENT DOCUMENTS

| | | | |
|---|---|---|---|
| 599,955 | 3/1898 | Beach | 604/331 |
| 2,182,702 | 12/1939 | Previn | 604/331 |
| 2,616,426 | 11/1952 | Gordon | 604/330 |
| 3,404,682 | 10/1968 | Waldron | 604/330 |
| 4,381,771 | 5/1983 | Gabbay | 604/330 |
| 4,412,833 | 11/1983 | Wiegner et al. | 604/14 |

FOREIGN PATENT DOCUMENTS 524582  8/1940 United Kingdom ............... 604/13

Primary Examiner—Jerome L. Kruter
Attorney, Agent, or Firm—Hovey, Williams, Timmons & Collins

[57] ABSTRACT

A device (1) for positioning within a human female vagina (V) to collect fluid discharged from the uterus (U), and also an instrument to facilitate positioning. The device (1) includes a receptacle (2) having a body (3) providing a collection chamber (4) for the fluid, and a rim (5) defining an inlet opening (6) into the chamber (4). The receptacle (2) is positioned within the vagina (V) so that the rim (5) surrounds the cervix (C) and the collection chamber (4) extends downstream so that fluid discharged from the uterus through the cervix (C) flows through the rim inlet opening (6) and is collected in the collection chamber (4). A trap valve (13) within the receptacle (2) permits the fluid to flow into the collection chamber (4) but inhibits return flow out of the receptacle (2).

20 Claims, 3 Drawing Sheets

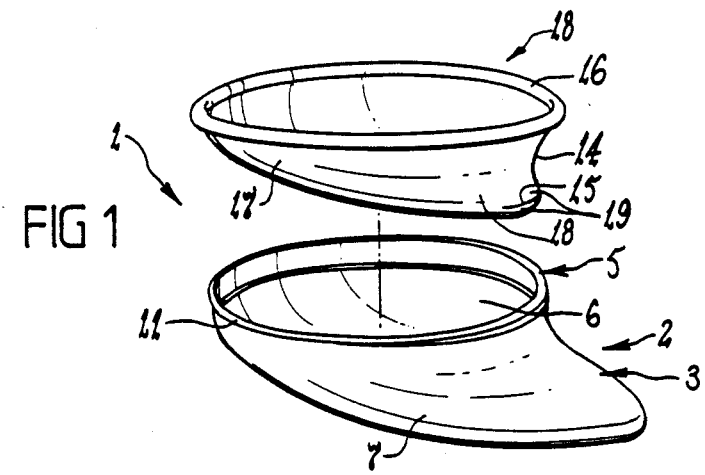
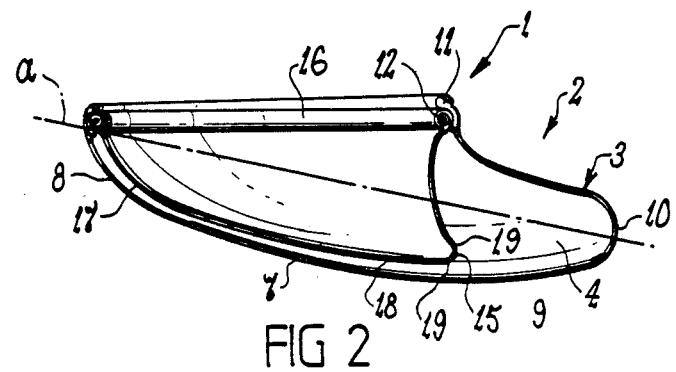
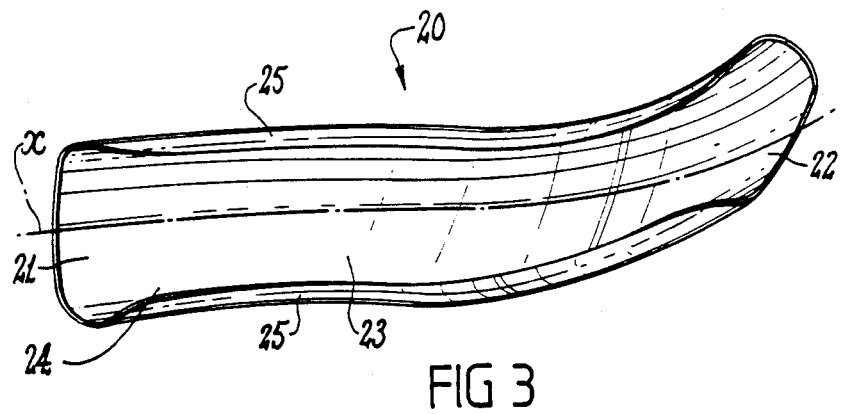

VALVED VAGINAL COLLECTION DEVICE

BACKGROUND OF THE INVENTION

1. Field of the Invention

This invention relates generally to the collection of human body discharge, and in particular to a device for positioning in the body for collecting waste fluid flowing along a body passage, and also to an instrument for positioning that receptacle in the body. The invention is applicable to the collection of menses flow, mucus discharge, and other discharge from female humans, particularly during a menstrual period. It will be convenient to hereinafter disclose the invention in relation to that exemplary application, although it is to be appreciated that the invention may not be limited to that application.

2. Description of the Prior Art

Menses flow from the uterus of female humans, discharged along the vagina and through the outlet orifice thereof, has traditionally been collected through the use of absorbent material. That material has been configured into a pad that can be positioned immediately over the outlet orifice to receive and absorb the menses discharged therethrough. Alternatively, that material has been configured into a tampon insertable into the vagina to receive and absorb the menses flow therealong. That tampon may be positioned within the vagina with the assistance of an applicator instrument.

With these pads and tampons, the absorbed menses tends to remain in contact with the body tissue of the wearer until the pad or tampon is removed. That contact may be uncomfortable for the pad or tampon wearer. Moreover, in some situations that contact may be unhygienic, possibly leading to tissue infection and/or toxicity. Removal and disposal of a used pad or tampon, involving hand contact with the absorbed menses, may also be unhygienic or unpleasant.

SUMMARY OF THE INVENTION

It is an object of the present invention to alleviate these disadvantages through the provision of a relatively simple device for collecting discharged body waste fluid, particularly menses. A further object of the present invention is to provide an instrument for positioning that device within the body for collecting the fluid.

With those objects in mind, the present invention broadly provides a device for positioning within a human female vagina to collect fluid discharged from the uterus, including a receptacle having a body providing a collection chamber for the fluid, and a rim defining an inlet opening into the collection chamber, the receptacle being constructed and arranged for positioning within the vagina so that the opening faces upstream toward the cervix with the collection chamber extending downstream therefrom whereby fluid discharged from the uterus through the cervix flows through the inlet opening and is collected in the collection chamber.

The present invention also broadly provides an instrument for positioning the above device within the vagina. That instrument is elongate with opposite leading and trailing end regions, and having a recess adjacent the leading end region for at least partially receiving and holding the device, the instrument being insertable in an elongate direction into the vagina with the leading end region leading until the device is adjacent a desired location, whereafter the instrument is removed from the vagina leaving the device in position for collecting fluid discharged from the uterus.

In the example application of the present invention, the device is preferably intended to be positioned within the vagina immediately adjacent the cervix of the uterus to receive menses flowing from the cervix passage, with the receptacle body extending from the rim along the vagina for collecting the menses within the collection chamber. The rim may be shaped and sized to encircle the cervix, with the cervix tending to enter the receptacle.

The receptacle preferably has an elongate collection chamber that will extend generally along the vagina during receptacle use. Moreover, the body is preferably flexible so that it can be generally configured to the shape and size of the vagina when positioned therein. In that regard, the body is preferably composed of flexible material.

The receptacle body is preferably connected to the rim to provide the chamber inlet opening. That opening is preferably at or toward one end of the elongate collection chamber.

The receptable rim is preferably of a slightly rigid or stiff construction so as to generally retain its shape and maintain communication through the inlet opening between the cervix and the collection chamber. This construction will also preferably assist in maintaining the flexible receptacle body in an orientation defining the collection chamber and so prevent total body collapse. The receptacle rim is preferably also of a resilient construction so that it may be deformed to faciliate positioning within the vagina.

Preferably, the device includes a trap valve for generally trapping received fluid therein, and inhibiting reverse flow of that fluid out of the chamber. This trap valve may particularly assist in retention of fluid within the chamber during receptacle removal following use.

The trap valve is preferably mounted within the receptacle so that fluid flowing into the chamber passes through the valve but is inhibited from return flow through the valve toward the rim and inlet opening. Thus, the fluid is trapped by the valve within the collection chamber.

The instrument for positioning the device preferably has an elongate passage extending at least substantially entirely therealong. That passage preferably provides the recess for holding the device. That passage preferably opens at the leading end region. The passage may also be open sided along the extent thereof. The flexible receptacle body and resilient rim will preferably collapse as necessary to fit within the recess thereby reducing the overall size of the instrument required to hold the device.

The instrument is preferably suitably shaped and sized relative to the vagina to enable insertion therealong in a manner facilitating device positioning therein. Specifically, that instrument is preferably shaped and sized to slide relatively easily along the vagina, the leading end region reaching the position for the device and at least a trailing end region not entering the vagina and thereby being accessible for gripping during instrument insertion and withdrawal. In the example application, the instrument will slide along the vagina until the leading end region is immediately adjacent the cervix of the uterus. To facilitate that insertion, the instrument is preferably of a curved rather than straight shape so as to negotiate the curved vagina and present the device to the cervix.

In using the instrument, once the device been correctly presented it will be possible to simply withdraw the instrument from the vagina disengaging it from the device to leave that device in its collecting position. That disengagement might conveniently be assisted with finger manipulation of the instrument and device.

BRIEF DESCRIPTION OF THE DRAWING FIGURES

The following description refers to a preferred embodiment of the device and applicator instrument of the present invention. To facilitate an understanding of the invention, reference is made in the description to the accompanying drawings where the device and instrument are illustrated. It is to be understood that the invention is not limited to the embodiment as hereinafter described and as illustrated.

In the drawings:

FIG. 1 is a perspective view of the device when unassembled according to a preferred embodiment of the present invention;

FIG. 2 is a cross-sectional side view of the device of FIG. 1, when assembled;

FIG. 3 is a perspective view of the applicator instrument according to a preferred embodiment of the present invention.

DESCRIPTION OF THE PREFERRED EMBODIMENTS

Figure 4:
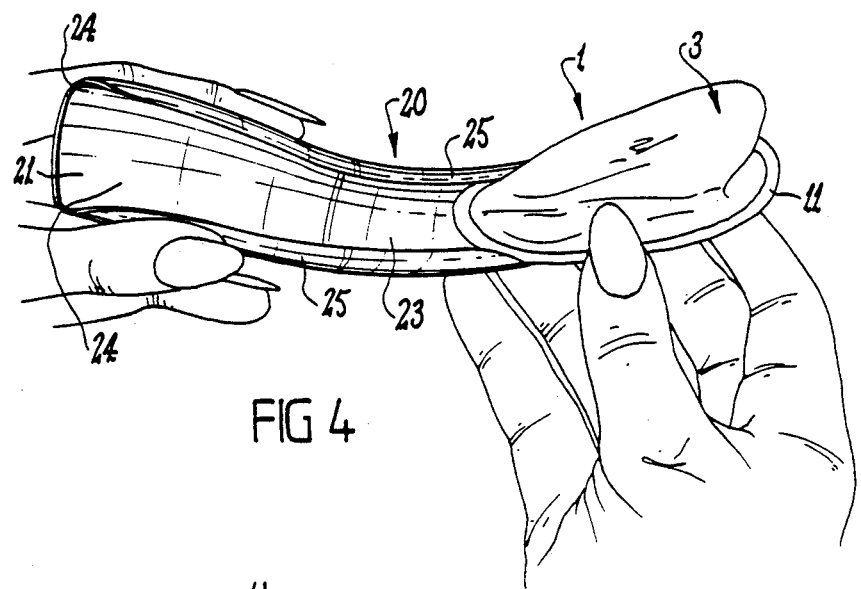
FIGS. 4 to 7 are side views showing the instrument of FIG. 3 within the vagina of a female human.

Referred initially to FIGS. 1 and 2 there is generally illustrated device 1, including receptacle 2. Receptacle 2, has body 3, providing collection chamber 4. Receptacle 2, also has rim 5, defining inlet opening 6, opening into chamber 4, so that, in device use fluid can flow into receptacle body 3, through opening 6, for collection within chamber 4.

Receptacle body 3, is formed of flexible thin material and is pouch-like in shape. In particular, body 3, is elongate and has thin wall 7, providing receiving section 8, extending from rim 5, and curving generally inwardly so as to be bowl shaped. Reduced collection section 9, emerges from receiving section 8, and projects somewhat laterally therefrom to closed terminal end 10. Thus collection chamber 4, will generally taper inwardly from adjacent rim 5, to closed terminal end 10, although it will be appreciated that the flexible nature of body 3, may well cause distortion of body 3, and chamber 4, particularly during device use.

Receptacle body 3, will provide chamber 4, of any suitable size depending on the intended application of device 1. In the example application, chamber 4, may have length of between about 100 and 150 millimeters and may taper from a diameter of between about 50 to 100 millimeters adjacent rim 5, to terminal end 10.

Receptacle body wall 7, may be smooth (as illustrated). Alternatively, wall 7, may be shaped so that it can be controllably collapsed for packaging and/or positioning in use, and then extended for collecting fluid during use. In particular, wall 7, may permit controlled folding so that wall 7, may be at least partly progressively collapsed toward rim 5, for packaging and positioning, and extended away from rim 5, during fluid collection. That may be achieved by providing wall 7, with a concertina type configuration.

Receptacle body 3, may be composed of any suitable flexible material. In the example application, body 3, may be composed of low density plastics material or rubber material, or other slightly resiliently, flexible material.

Receptacle rim 5, is connected to body wall 7, so as to lie in a plane that is angled, relative to general longitudinal axis a, of body 3. In the example application, that rim plane will lie at an acute angle to axis a, so that, when device 1, is in position, rim 5, upstands from receptacle body 3, with inlet opening 6, facing upwardly and receptacle body 3, depending somewhat leterally therefrom (as illustrated in FIG. 2).

Rim 5, is formed integral with body 3. Rim 5, and body 3, may be composed of the same material. However, rim 5, may conveniently incorporate thickened rib 11, for increasing rigidity and resilience within rim 5, so that rim 5, holds inlet opening 6, in a desired shape during use.

In addition, device 1, includes resilient member 12, located at rim 5, to assist in maintaining opening 6, in that desired shape during use. Member 12, will not be so rigid as to prevent resilient distortion or deformation of rim 5, to facilitate insertion for use and removal after use. Member 12, may be an endless coil spring and rim 5, may extend partly about and over that member 12, so as to grip same. Rib 11, will assist retention of member 12, within rim 5, and for that purpose rib 11, may be of greater cross-sectional size adjacent collecting section 9, for supporting body 3, when holding fluid in chamber 4. Member 12, may be removable from rim 5, to allow cleansing of device 1.

Rim 5, is generally circular in shape. Inlet opening 6, will have a diameter selected according to the intended application of device 1, and in the example application that may be between about 50 and 100 millimeters, typically about 60 millimeters.

Device 1, also includes trap valve 13, which, in device use, is located within receptacle 2, to trap fluid received within chamber 4, and inhibit accidental return flow therefrom. Trap valve 13, includes valve diaphragm 14. Diaphragm 14, extends across collection chamber 4, and has small aperture 15, therein through which fluid can flow diaphragm 14, being arranged so that fluid can freely flow through aperture 15, toward terminal end 10, but is inhibited in reverse flow from chamber 4, through aperture 15, toward inlet opening 6.

Diaphragm 14, is formed of flexible thin material and is also generally pouch-like in shape similar to, but smaller than receptacle 2. Diaphragm 14, has peripheral edge 16, through which diaphragm 14, is connected to receptacle 2, at rim 5. Diaphragm 14, also has receiving region 17, extending from edge 16, and arriving generally forwardly so as to be shallow bowl shaped. Receiving region 17, closely nests with receiving section 8, of body 3, in device use. Tip region 18, emerges somewhat laterally from receiving region 17, and projects into collection section 9, in device use. Tip region 18, terminates in a pair of flexible lips 19, defining slit shaped aperture 15, facing toward terminal end 10. Lips 19, flex toward and away from one another to respectively close and open aperture 15.

Valve diaphragm 14, may be formed integral with receptacle 2, (not illustrated). Alternatively, diaphragm 14, may be separately fabricated and connected to receptacle 2, (as illustrated). In that regard, peripheral edge 16, is connected to resilient member 12, by enclosing member 12, within edge 16.

Valve diaphragm 14, may be conveniently composed of the same material as receptacle 2.

Although not illustrated, device 1, may also include a gripping line extending from receptacle 2, that can be readily gripped to enable device retrieval. That line may be inextensible and may be formed integral with receptacle body 3, or separately fabricated and connected thereto.

Turning now to FIG. 3, there is generally illustrated instrument 20, used to position device 1, for use. Instrument 20, is rigid and elongate with opposed leading end region 21, and trailing end region 22. Passage 23, extends along instruments 20, and opens through end regions 21,22. In addition, passage 23, also opens laterally so as to provide side opening 24, extending between end regions 21,22.

Instrument 20, is thin walled and of a somewhat flattened cross-sectional shape, and conveniently may be generally C-shaped. As such, passage 23, is of an oval or narrow slot-like shape, with wide side opening 24, leaving curled longitudinal edge regions 25.

Instrument 20, is longitudinally curved between end regions 21,22, to facilitate sliding along the vagina and also correct positioning of device 1, in use. That curvature is such as to produce a curved spiral within instrument 20, between the end regions 21,22. That is, instrument 20, not only has a helical spiral about an elongate central axis x, but that axis x, is also curved. The spiral causes a relative rotary displacement of instrument regions 21,22, of about 80°. The curve is such that central axis x, extends along a shallow arc with side opening 24, facing generally radially inwardly of that arc.

Instrument 20, is further shaped at least at leading end region 21, by removal of sharp corners from edges 25. This will facilitate insertion into the vagina and minimise injury through contact with vagina walls.

Instrument 20, may be manufactured from any suitable material using any suitable manufacturing process. In the example application, instrument 20, may be molded from plastics material, and/or fabricated from paper board or card board suitable coated (such as with wax) to retain its rigidity in use.

Referring now to FIGS. 4 to 7, use of device 1, and instrument 20, will now be outlined in relation to the example application. Initially, assembled device 1, may be manually loaded into passage 23, of instrument 20, by an intending user. Loading is achieved by radially compressing rim 5, so that device 1, can be positioned and held in passage 23, adjacent end region 21. In that regard, device 1, may be either fed along passage 23, (as illustrated in FIG. 4) or may be passed through side opening 24, (not illustrated).

Compressed rim 5, is resiliently urged to resume an uncompressed shape and so is caught within passage 23, by edges 25. Device 1, is positioned in passage 23, so that rim 5, faces outwardly of the curve of instrument 1, and away from side opening 24. Receptacle 2, will extend out through side opening 24, of passage 23.

In an alternative embodiment (not illustrated) device 1, may be preloaded into instrument 20, during manufacture and packaging. That may be particularly suitable where it is intended that instrument 20, will be disposed of following positioning of device 1, held thereby.

Figure 5:
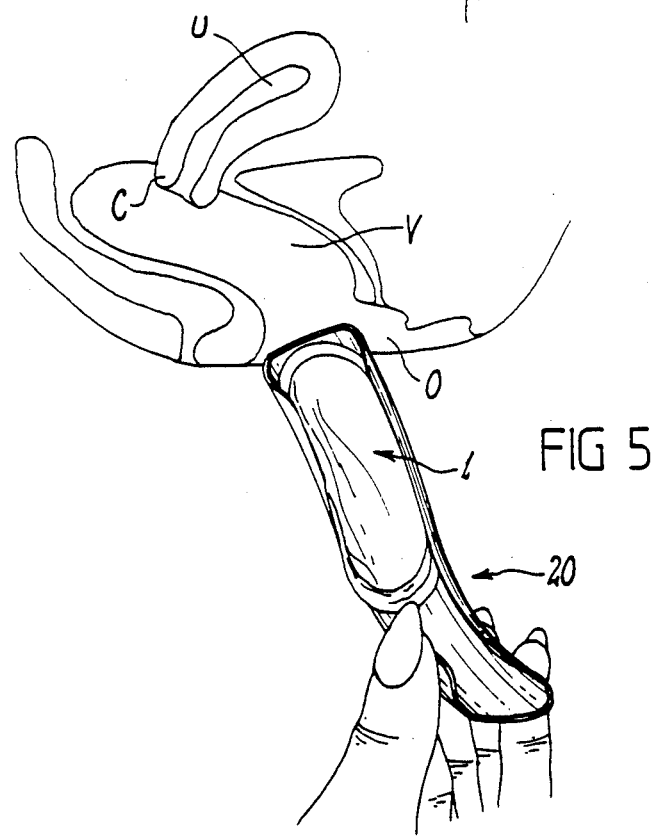

To position device 1, within a vagina, instrument 20, is initially manually presented to outlet orifice O, of vagina V, (as diagramatically illustrated in FIG. 5). In that presentation, leading end region 21, lies in the symmetry plane of the user and instrument 20, curves in an upward direction toward trailing end region 22.

Instrument 20, is then gently plunged into vagina V, leading end region 21, moving progressively therealong toward cervic C. During that movement, successive regions of instrument 20, passing through outlet orifice O, are maintained in the symmetry plane. Because of the twist along instrument 20, that causes instrument 20, to slowly rotate about elongate axis x. Progressively, that rotation reorientates instrument 20, so that it curves downwardly from leading end region 21, to trailing end regions 22, to follow the vagina curvature.

Rotation of instrument 20, also rotates device 1, therewith so that when leading end region 21, reaches cervix C, rim 5, is beneath and faces toward that cervix C. Thus, insertion of instrument 20, automatically brings device 1, adjacent to its position for collecting menses flow from uterus U.

Figure 6:
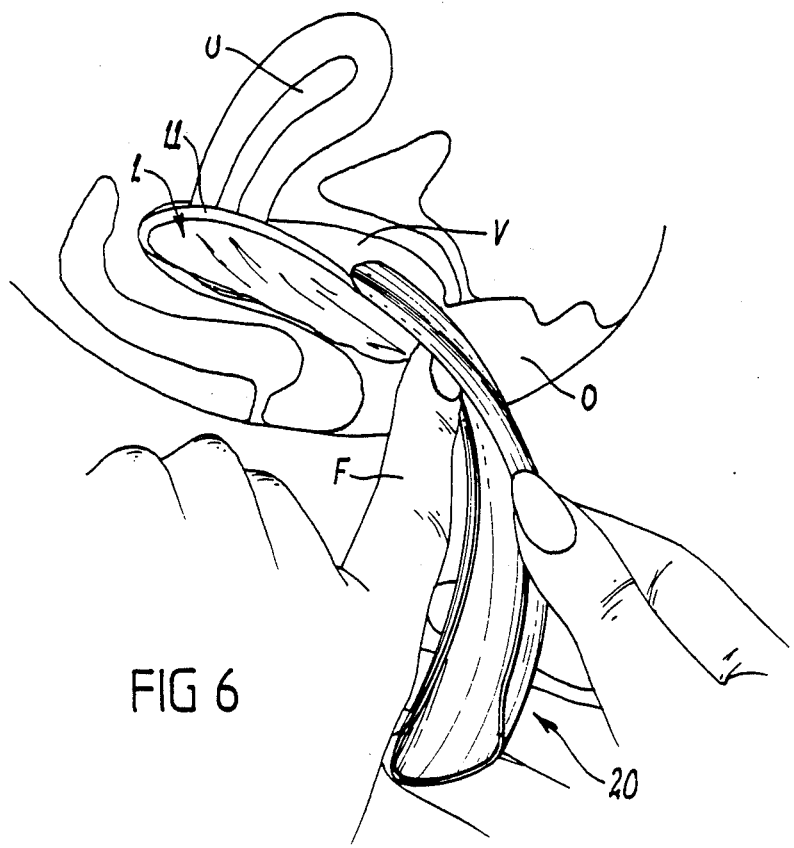
Figure 7:
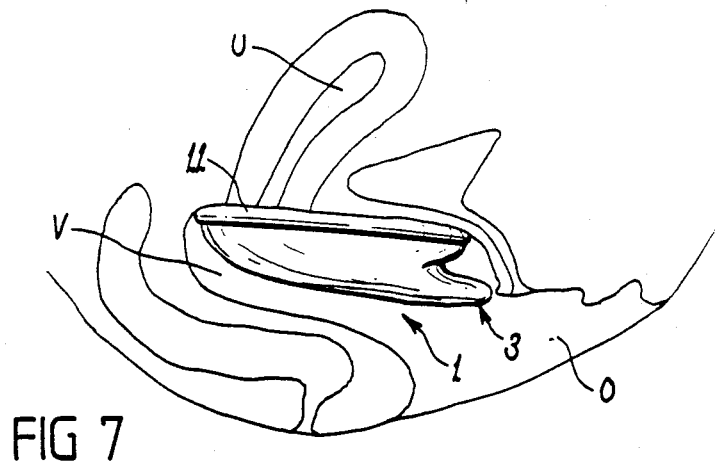

Thereafter, a finger F, is slid along passage 23, to engage device 1, and instrument 20, is slowly withdrawn from vagina V, (as illustrated in FIG. 6). During this movement device 1, is ejected from passage 23, but not significantly moved relative to vagina V, or cervix C. Thus, as instrument 20, leaves passage 23, resilient rim 5, expands to resume its normal shape so as to encircle cervix C, with rim 5, extending to the posterior fornex (as illustrated in FIG. 7). A natural suction effect should then result in an excellent seal between rim 5, and the wall of vagina V, surrounding cervix C, so as to positively locate device 1.

During a menstrual period, menses from uterus U, passes through cervix C, directly into device 1, for trapped collection within chamber 4. Thus, the menses does not move down through vagina V, in contact with the body tissues thereof. As collection chamber 4, receives menses receptacle body 3, may progressively drop along vagina V.

To withdraw device 1, body 3, is gripped at terminal end 10, and generally pulled so that device 1, is dislodged from adjacent cervix C, and moved along vagina V, through outlet orifice O. Because of diaphragm 14, collected menses is retained within chamber 4, during that withdrawal. Device 1, may then be disposed of in a suitable manner, or cleansed for reuse.

A device according to the present invention when used in the exemplary application, minimises contact between menstrual period menses and the body tissues, particularly those of the vagina. This may reduce the possibility of body tissue infection due to that contact, and may be generally more hygienic than the traditional use of absorbent material formed into pads and tampons. In any event, that lack of contact may improve comfort for the user during a menstrual period.

Other advantages of the device include protection of a user against toxic shock syndrome known to be associated with tampon use, protection of a user against sexually transmitted disease because of the sealing effect about the cervix, and protection of a user against cervical cancer risk, urinary tract infection, and haemorrhoids.

Because the device provides a vaginal barrier, it may also be used as a barrier method of contraception, particularly in association with optional use of spermicide.

An instrument according to the present invention permits easy and rapid positioning of the device of the present invention. The instrument is relatively simple so that its purchase cost may be minimal.

Finally it is to be appreciated that various modifications and/or alterations may be made to the device and instrument without departing from the ambit of the present invention defined in the claims appended hereto.

I claim:

1. A catamenial device for positioning entirely within a human female vagina to collect fluid discharge from the uterus at all positions of the body of the wearer, comprising:

a receptacle having a thin-walled body providing a collection chamber and a rim on the body forming an inlet opening into the collection chamber through which fluid passes into the collection chamber, the body including— a receiving section extending from the rim and curving inwardly so as to be generally shallow bowl-shaped, and a reduced collection section emerging generally laterally from the receiving section and in which fluid is collected, and trap valve means within the collection chamber between the inlet opening and the collection section for trapping fluid in the collection section, said trap valve means including a peripheral edge through which said valve means is connected to the rim of the body and a receiving region curving from the peripheral edge into the collection chamber so as to be generally shallow bowl-shaped and nest within the receiving section of the receptacle body, the trap valve also including a tip region emerging from the receiving region and projecting into the collection section of the receptacle body, said trap valve means having an aperture in the tip region that opens for fluid flow into the collection section but closes to inhibit fluid flow out of the collection section;

the device including structure for operative positioning entirely within the vagina so that the rim surrounds the cervix with the cervix being received in the inlet opening and the body extending down the vagina therefrom, and for fluid discharge from the uterus through the cervix and into the collection chamber and through said trap valve aperture to be collected in the collection section of the receptacle body, said trap valve means including means for preventing escape of said fluid discharge from said collection section during removal of said device from the vagina and at all positions of the body of the wearer.

2. A device as claim in claim 1, wherein the trap valve includes a valve diaphragm composed of resiliently flexible material and the aperture is closed slit-shaped, so that in device use fluid flowing from the cervix to the aperture flexes the diaphragm to open the slit-shaped aperture and allow passage of the fluid therethrough into the collection section.

3. A device as claimed in claim 2, wherein the diaphragm includes a pair of flexible lips between which is defined the slit-shaped aperture, the flexible lips pressing against one another and moving away from one another to respectively close and open the aperture.

4. A device as claimed in claim 1, wherein the trap valve is removably locatable within the body to permit cleansing of the device.

5. A device as claimed in claim 1, wherein the receptacle generally tapers inwardly from the inlet opening toward a closed terminal end remote from the inlet opening.

6. A device as claimed in claim 1, wherein the receptacle body is composed of flexible material and the rim has a thickened rib for stiffening the rim and thus holding the inlet opening in a predetermined shape.

7. A device as claimed in claim 6, wherein the rim is ring-shaped so as to provide a round inlet opening for fitting about the cervix in device use, and the rim is resiliently flexible for resilient deformation from the ringshape to facilitate insertion into, and retrieval from the vagina.

8. A device as claimed in claim 7, wherein the rim opening extends in a plane that is acutely angled relative to the receptacle body, so that in device use the rim upstands from the receptacle body with the upwardly facing opening extending about the cervix and the receptacle body extending down the vagina.

9. A device as claimed in claim 7, wherein the inlet opening has a diameter of between about 50 and 100 mm.

10. A device as claimed in claim 1, and further comprising a resilient member for resiliently urging the rim to hold the inlet opening in a predetermined shape.

11. A device as claim 10, wherein the resilient member is a coil spring extending along the rim.

12. A device as claimed in claim 10, wherein the resilient member is removable from the rim to permit cleansing of the device.

13. A one-piece instrument for entirely positioning the device as claimed in claim 1, within a human female vagina to collect fluid discharged from the uterus, the instrument being elongate with opposite leading and trailing end regions, and being generally C-shaped in cross-sectional profile thereby providing an open-sided elongate passage extending therealong for at least partially receiving and holding the device adjacent the leading end region, the instrument also being helically spiralled about a central elongate axis between the opposite end regions, the instrument being insertable in an elongate direction into the vagina with the leading end region leading until the device is adjacent a desired location, whereafter the instrument is removed from the vagina leaving the device in position for collecting fluid discharged from the uterus.

14. An instrument as claimed in claim 13, wherein the instrument has an elongate passage extending at least substantially entirely therealong and which provides the recess for holding the device.

15. An instrument as claimed in claim 14, wherein the instrument is generally C-shaped in cross-sectional profile thereby providing an open sided elongate passage.

16. An instrument as claimed in claim 13, wherein the instrument is helically spiralled about a central elongate axis between the opposite end regions of the instrument.

17. An instrument as claimed in claim 13, wherein the instrument is spiralled about 80° between the opposite end regions of the instrument so that the end regions are angularly offset one from another by an included angle of about 80°.

18. An instrument as claimed in claim 17, wherein the instrument is also longitudinally curved so that a central elongate axis extends along a shallow arc and the recess opens radially inwardly of the arc.

19. An instrument as claimed in claim 13, wherein the instrument is longitudinally curved so that a central elongate axis extends along an arc.

20. An instrument as claimed in claim 19, wherein the central elongated axis extends along a shallow arc and the recess opens radially inwardly of the arc.

* * * * *